United States Patent

Weisburg et al.

Patent Number: 5,324,632
Date of Patent: Jun. 28, 1994

[54] NUCLEIC ACID PROBES AND METHODS FOR DETECTING FUNGI

[75] Inventors: William G. Weisburg, Milford, Mass.; Susan M. Barns, Bloomington, Ind.; Dale A. Pelletier, Brighton; Mitchell L. Sogin, Falmouth, both of Mass.

[73] Assignee: Amoco Corporation, Naperville, Ill.

[21] Appl. No.: 780,800

[22] Filed: Oct. 22, 1991

Related U.S. Application Data

[63] Continuation of Ser. No. 420,577, Oct. 12, 1989, abandoned.

[51] Int. Cl.[5] .......................... C12C 1/68; C07H 21/04
[52] U.S. Cl. ........................................ 435/6; 536/24.3; 536/24.32; 536/24.33
[58] Field of Search ................... 536/27, 24.3, 24.33, 536/24.32; 435/6

[56] References Cited

U.S. PATENT DOCUMENTS 4,851,330 7/1989 Kohne .................................... 435/6

FOREIGN PATENT DOCUMENTS 0272009 6/1988 European Pat. Off. .
8803957 6/1988 PCT Int'l Appl. .

OTHER PUBLICATIONS

Nucleic Acid Sequence Printout (Aug. 17, 1992), pp. 1-9.
Matthews et al. Analytical Biochem. 169: 1-25, 1988 (Feb. 1988).
Cooper et al. in "Manual of Clinical Microbiology" ed. Lennette, E. H. pp. 526-541, 1985.

Primary Examiner—Margaret Parr
Assistant Examiner—Paul Tran
Attorney, Agent, or Firm—Joanne M. Giessner

[57] ABSTRACT

Nucleic acid probes are described for detecting fungi capable of causing fungal septicemia or capable of causing food spoilage. The preferred probes are complementary to ribonucleic acid sequences found in numerous fungi and absent in animal or plant genomes. As such, these probes can detect the rRNA, rDNA, or polymerase chain reaction amplification products from the majority of fungal species. The detection of etiological agents of human fungemia, the clinical diagnosis of this disease and the direct evaluation of food or beverage fungal content utilizing rRNA or rDNA probes is now possible.

16 Claims, 1 Drawing Sheet

FIGURE
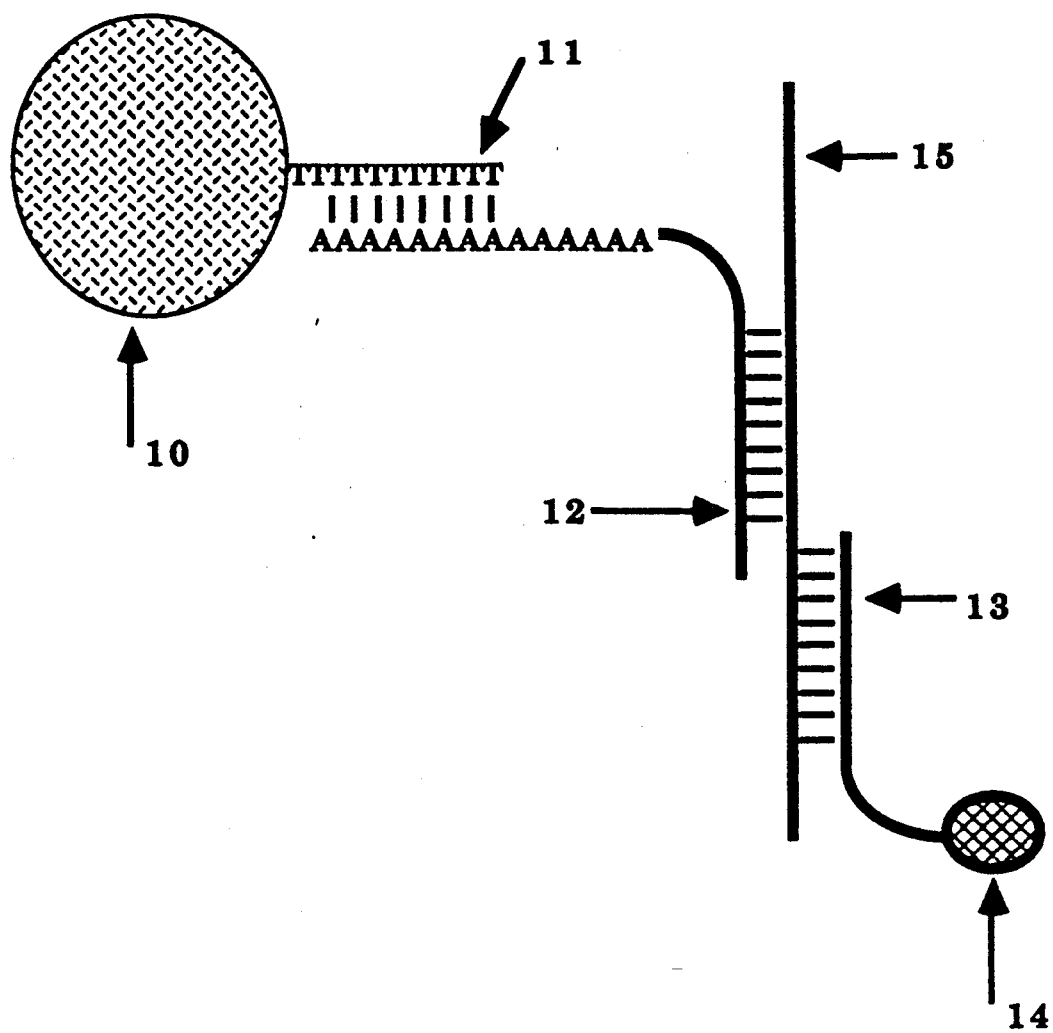

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TGTCTGGACC TGGTGAGTTT CCCCGTG                                27

( 2 ) INFORMATION FOR SEQ ID NO: 2:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TGTCTGGACC TGGTGAGTTT CCCCGTGTTG AGTCAAATT                   39

( 2 ) INFORMATION FOR SEQ ID NO: 3:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 3:

TCCTCGTTAA GGGATTTAAA TTGTACTCAT TCCAATT                     37

( 2 ) INFORMATION FOR SEQ ID NO: 4:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TCCTCGTTAA GGTATTTACA TTGTACTCAT TCCAATT                     37

( 2 ) INFORMATION FOR SEQ ID NO: 5:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TCCTCGTTAA GGTGTTTAAA TTGTACTCAT TCCAATT                     37

( 2 ) INFORMATION FOR SEQ ID NO: 6:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO: 6:

AACTAAGAAC GGCCATGCAC CACCAT                                 26

( 2 ) INFORMATION FOR SEQ ID NO: 7:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TGGTGCCCTT CCGTCAATTT CTTTAAGTTT CAGCCTTGCG                  40

( 2 ) INFORMATION FOR SEQ ID NO: 8:

( i ) SEQUENCE CHARACTERISTICS:
    ( A ) LENGTH: 48
    ( B ) TYPE: nucleic acid
    ( C ) STRANDEDNESS: single
    ( D ) TOPOLOGY: linear ( x i ) SEQUENCE DESCRIPTION: SEQ ID NO: 8:

TCGCTGGCGC AAGGCCATGC GATTCGAGAG GTTATTATGA ATCATCAG    48

( 2 ) INFORMATION FOR SEQ ID NO: 9:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( x i ) SEQUENCE DESCRIPTION: SEQ ID NO: 9:

CAAGCTGATG ACTTGTGCTT ACTAGGGATT    30

( 2 ) INFORMATION FOR SEQ ID NO: 10:

( i ) SEQUENCE CHARACTERISTICS:
    ( A ) LENGTH: 37
    ( B ) TYPE: nucleic acid
    ( C ) STRANDEDNESS: single
    ( D ) TOPOLOGY: linear ( x i ) SEQUENCE DESCRIPTION: SEQ ID NO: 10:

TCGGCATAGT TTGTGGTTAA GACTACGACG GTATCTT    37

( 2 ) INFORMATION FOR SEQ ID NO: 11:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( x i ) SEQUENCE DESCRIPTION: SEQ ID NO: 11:

AAATGCTTTC GCAGTAGTTG GTCTT    25

( 2 ) INFORMATION FOR SEQ ID NO: 12:

( i ) SEQUENCE CHARACTERISTICS:
    ( A ) LENGTH: 49
    ( B ) TYPE: nucleic acid
    ( C ) STRANDEDNESS: single
    ( D ) TOPOLOGY: linear ( x i ) SEQUENCE DESCRIPTION: SEQ ID NO: 12:

AAATGCTTTC GCAGTAGTTG GTCTTCGGTA AATCCAAGAA TTTCACCTT    49

( 2 ) INFORMATION FOR SEQ ID NO: 13:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( x i ) SEQUENCE DESCRIPTION: SEQ ID NO: 13:

ACGTCCTATT TTATTATTCC ATGCTAAT    28

( 2 ) INFORMATION FOR SEQ ID NO: 14:

( i ) SEQUENCE CHARACTERISTICS:
    ( A ) LENGTH: 29
    ( B ) TYPE: nucleic acid (C) STRANDEDNESS: single
(D) TOPOLOGY: linear (xi) SEQUENCE DESCRIPTION: SEQ ID NO: 14:

AAGTCATATT TCATTATTCC ATGCTAACT                       29

(2) INFORMATION FOR SEQ ID NO: 15:

(i) SEQUENCE CHARACTERISTICS:
(A) LENGTH: 28
(B) TYPE: nucleic acid
(C) STRANDEDNESS: single
(D) TOPOLOGY: linear (xi) SEQUENCE DESCRIPTION: SEQ ID NO: 15:

TCGTCGAGTT ATGTTATTCC ATGCAAAT                        28

(2) INFORMATION FOR SEQ ID NO: 16:

(i) SEQUENCE CHARACTERISTICS:
(A) LENGTH: 35
(B) TYPE: nucleic acid
(C) STRANDEDNESS: single
(D) TOPOLOGY: linear (xi) SEQUENCE DESCRIPTION: SEQ ID NO: 16:

CCGAATTCGT CGACAACCTG GTTGATCCTG CCAGT                35

(2) INFORMATION FOR SEQ ID NO: 17:

(i) SEQUENCE CHARACTERISTICS:
(A) LENGTH: 39
(B) TYPE: nucleic acid
(C) STRANDEDNESS: single
(D) TOPOLOGY: linear (xi) SEQUENCE DESCRIPTION: SEQ ID NO: 17:

CCCGGGATCC AAGCTTGATC CTTCTGCAGG TTCACCTAC            39

NUCLEIC ACID PROBES AND METHODS FOR DETECTING FUNGI

CROSS REFERENCE TO RELATED APPLICATION

This application is a continuation of application Ser. No. 420,577, filed Oct. 12, 1989, now abandoned.

FIELD OF THE INVENTION

This invention relates to the detection of fungal organisms. More specifically, it provides nucleic acid probes and compositions along with methods for their use for the specific detection of yeasts and molds in clinical, food, environmental and other samples.

BACKGROUND OF THE INVENTION

The fungi are a diverse collection of cell-wall enclosed eukaryotes either saprophytic or parasitic and may be morphologically described as yeasts, molds, mushrooms, or by other names. They are ubiquitous organisms, mostly innocuous, sometimes used for commercial purposes, and occasionally pathogenic.

The pathogenic fungi are included within the domain of medical mycology. This medical field recognizes categories of fungal pathogens (see Rippon, J. W., Medical Mycology, Saunders Co., Philadelphia, 1988, for example) including superficial, cutaneous, subcutaneous, and systemic infection. By far the most serious pathology caused by the fungi that clinicians face are the systemic infections. Deep tissue and systemic fungemia claim high mortality rates, particularly among immune-compromised populations.

Among the fungi capable of causing systemic fungemia, there is a dichotomy between the so-called "pathogenic" fungi and the "opportunistic" fungi. It is a deceptive nomenclature; the opportunists are the killers, and the pathogenic fungi are often self-limiting. The pathogenic fungi include *Coccidioides immitis, Histoplasma capsulatum, Blastomyces dermatitidis, Paracoccidioides brasiliensis*, and the subcutaneous pathogen, *Sporothrix schenkii*. The important opportunistic fungi include the Candidas—particularly *C. albicans, C. tropicalis, C. parapsilosis*, and *Torulpsis (Candida) glabrata*—*Cryptococcus neoformans*, members of the genus Aspergillus, and to a lesser extent, practically any fungus that can survive at host physiological temperatures.

Clinical diagnosis and treatment of systemic fungemia suffers several shortcomings compared to bacterial septicemia (which often occurs in the same immune-deficient population). First, antifungal chemotherapy is more toxic to the patient than analogous antibacterial chemotherapy. As a result, clinicians desire a more reliable demonstration of fungemia before prescribing antifungal agents. Second, fungemic patients have a poor prognosis, unless diagnosed early in infection. Third, fungi generally grow slower than the major barceremic organisms, and consequently diagnosis requiring an in vitro culture step is time consuming. And fourth, some of the fungi (again in diagnoses requiring in vitro cultivation) will not yield colonies on synthetic media for weeks, if at all. All of these factors, plus the fact that a wide array of fungi are potential systemic pathogens, point to the need for a direct method of fungal detection inclusive for virtually all fungi.

It is an aspect of the present invention to provide nucleic acid probes capable of detecting fungi.

It is another aspect of the present invention to provide nucleic acid probes which can hybridize to target regions which can be rendered accessible to probes under normal assay conditions.

It is yet another aspect to provide nucleic acid probes to fungal rRNA sequences useful as the basis for rapid diagnostic assays for assessing the presence of these organisms in a clinical sample.

While Kohne et al. (Biophysical Journal 8:1104–1118, 1968) discuss one method for preparing probes to rRNA sequences, they do not provide the teaching necessary to make probes to detect fungi.

Pace and Campbell (Journal of Bacteriology 107:543–547, 1971) discuss the homology of ribosomal ribonucleic acids from diverse bacterial species and a hybridization method for quantitating such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to prokaryotic systematics. These references, however, fail to relieve the deficiency of Kohne's teaching with respect to fungi, and in particular, do not provide specific probes useful in assays for detecting fungemia or its etiological agents, a broad spectrum of yeast and molds.

Hogan, et al (International Patent Application, Publication Number WO 88/03957) describe four putative fungal specific probes. None of them appear widely inclusive for fungi, nor are they related to the probes of the present invention.

Ribosomes are of profound importance to all organisms because they serve as the only known means of translating genetic information into cellular proteins, the main structural and catalytic elements of life. A clear manifestation of this importance is the observation that all cells have ribosomes.

Bacterial ribosomes contain three distinct RNA molecules which, at least in *Escherichia coli*, are referred to as 5S, 16S and 23S rRNAs. In eukaryotic organisms, there are four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 18S, 28S, and 5.8S rRNA are commonly used as generic names for the homologous RNA molecules in any eukaryote, and this convention will be continued herein.

It is another aspect of the present invention to provide nucleic acid probes complementary to unique nucleic acid sequences within the 18S ribosomal ribonucleic acid (rRNA) of fungal pathogens.

As used herein, probe(s) refer to synthetic or biologically produced nucleic acids (DNA or RNA) which, by design or selection, contain specific nucleotide sequences that alloy them to hybridize under defined predetermined stringencies, specifically (i.e., preferentially, see next paragraph) to target nucleic acid sequences. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescein, 32-P, biotin, etc.), or to facilitate their capture onto a solid support (e.g., polydeoxyadenosine "tails"). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion (one oriented 5' to 3', the other 3' to 5') to form a double-stranded nucleic acid with specific and stable hydrogen bonds, following explicit rules pertaining to which nucleic acid bases may pair with one another. The high specificity of probes relies on the low statistical probability of unique sequences occurring at random as dictated by the multiplicative product of their individual probabilities. These concepts are well understood by those skilled in the art.

The stringency of a particular set of hybridization conditions is determined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar NaCl.

All references made herein are fully incorporated by reference.

SUMMARY OF THE INVENTION

In accordance with the various principles and aspects of the present invention, there are provided nucleic acid probes and probe sets comprising deoxyribonucleic acid (DNA) or ribonucleic acid (RNA) sequences which hybridize, under specific conditions, to the ribosomal RNA molecules (rRNA), specifically 18S rRNA molecules, or rRNA genes (rDNA) of fungi but which do not hybridize, under the same conditions, to the rRNA or rDNA of bacteria or the host or environmental matrix which may be present in test samples. The probes of the present invention now permit the development of a valuable nucleic acid hybridization assay for the specific detection of fungemia or its etiological agents. This assay may advantageously be used to test for yeasts and molds in clinical samples of blood, urine, cerebrospinal fluid, skin biopsy, saliva, synovial fluid, sputum, bronchial wash, bronchial lavage, or other tissue or fluid samples from human patients or veterinary subjects.

The probes of the present invention also provide the basis for the development of valuable nucleic acid hybridization assays capable of detecting yeasts and molds associated with food spoilage. Most preferred probes of the present invention can hybridize to a diverse collection of fungi while not cross-reacting, at predetermined conditions, with meats, dairy products, grains, nuts, juices, and other commercial food matrices.

Nucleic acid hybridization based assays have been discovered to impart enhanced performance capabilities with respect to most currently available, microbiological or immunological methods for detection of fungi in test samples, generally including:
 a) increased sensitivity; i.e., the ability to detect yeast or mold in a given sample more frequently;
 b) potentially significant reductions in assay cost due to the use of inexpensive reagents and reduced labor;
 c) accurate identification of even biochemically unusual strains of the target organism, or isolates with dramatically different antigenic properties;
 d) direct assay for the presence of the yeast or mold and consequent potential to quantify the etiological agents;
 e) direct testing allows the monitoring of the efficacy of an antifungal regime; and
 f) potentially significant reductions in the exposure of laboratory technologists to bodily fluid specimens harboring infectious agents.

It has been discovered that other advantages incurred by directing the probes of the present invention against rRNA include the fact that the rRNAs detected constitute a significant component of cellular mass. Although estimates of cellular ribosome content vary, actively growing fungal cells may contain upwards of 100,000 ribosomes per cell, and therefore 100,000 copies of each of the rRNAs (present in a 1:1:1:1 stiochiometry in ribosomes). In contrast, other potential cellular target molecules such as genes or RNA transcripts thereof, are less ideal since they are present in much lower abundance. A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

The discovery that probes could be generated with the extraordinary inclusivity and exclusivity characteristics of those of the present invention with respect to the detection of virtually all fungal organism, without necessarily incurring cross-reactivity to animal, plant, or bacterial genomes was unpredictable and unexpected.

BRIEF DESCRIPTION OF THE TABLES

Further understanding of the principles and aspects of the present invention may be made by reference to the tables wherein:

Tables 1, 2, and 3 display the hybridization behavior of fifteen probes toward a panel of clinically and environmentally representative fungal species. Additional fungi were added to the panel in order to represent the breadth of known fungal taxa. Approximately eighty fungal species are represented, and the highest prevalence pathogens are represented by numerous strains. In addition, nucleic acids from a variety of non-fungal organisms are included for comparison including RNAs from human, wheat, normal human stool, and two ubiquitous bacterial species. Those skilled in the art understand that bacteria are so evolutionarily distant as to not generally cross-react with the types of probes described herein. It will be further recognized that the sequence variation among vertebrate animals and among higher plants is sufficiently narrow that an individual sample, such as wheat, has high predictive value.

All species on the panel are represented by 100 ng of purified, denatured RNA. Probes were 32-Phosphorous labelled, hybridized to panels under standard conditions, at the temperatures indicated, and autoradiographically evaluated. "+" represents strong hybridization signal after three hours exposure, "+ −" is a weak signal, "+ − −" is virtually absent, and "−" is indicative of no hybridization of probe to target. "NT" indicates that a particular probe was not tested against the designated strain.

BRIEF DESCRIPTION OF THE FIGURE

Still further understanding may be had by study of the accompanying FIGURE which shows a schematic representation of a dual probe capture/detector assay.

DETAILED DESCRIPTION OF THE INVENTION AND BEST MODE

Probe Development Strategy

The first step taken in the development of the probes of the present invention involved identification of regions of the 18S rRNA which potentially could serve as target sites for fungal specific nucleic acid probes. This entailed finding sites which are:

1) highly conserved (few nucleotide changes, deletions, or insertions) among the fungal rRNA sequences, and
2) substantially different in non-fungal (bacteria, human, or plant) rRNA sequences.

For this analysis, precise alignments of available 18S rRNA sequences were developed. A number of 18S rRNA sequences were determined as part of this effort. Such nucleotide sequences were determined by standard laboratory protocols either by cloning and sequencing of genes specifying rRNAs or by direct sequencing of the rRNAs themselves using reverse transcriptase (Lane, et al, 1985, Proceedings of the National Academy of Sciences, USA 82:6955–6959).

A computer algorithm, operating on the aligned set of 18S rRNA sequences, was used to identify regions of greatest similarity among the fungi. Nucleic acid probes to such regions will hybridize most widely among diverse fungi. Additional information was gained by comparing these fungal conserved regions to known 18S rRNA sequences from human, rat, mouse, corn, soy, rice, bacteria, protozoa, algae, etc.

Fifteen probes were identified, based on these analyses. The discovery of a specific type of non-fungal cross-reactivity does not necessarily render a probe uninteresting. For example, cross-reaction of a probe with the plant kingdom does not detract from the probe's usefulness in screening vertebrate blood for fungemia. Other probes described herein are known to cross-react, but they were designed to be employed in dual probe assays (see the FIGURE and Example 2).

Description of the Probes

As indicated, the above probe selection strategy yielded fifteen probes useful for hybridization to fungi in samples comprising:

PROBE 1417: 5'-TGTCTGGACCTGGT-GAGTTTCCCCGTG-3' (SEQ. ID NO: 1)

PROBE 1418: 5'-TGTCTGGACCTGGT-GAGTTTCCCCGTGTTGAGTCAAATT-3' (SEQ. ID NO: 2)

PROBE 1415: 5'-TCCTCGTTAAGGGATT-TAAATTGTACTCATTCCAATT-3' (SEQ. ID NO: 3)

PROBE 1416: 5'-TCCTCGTTAAGGTATT-TACATTGTACTCATTCCAATT-3' (SEQ ID NO: 4)

PROBE IG707: 5'-TCCTCGTTAAGGTGTT-TAAATTGTACTCATTCCAATT-3' (SEQ ID NO: 5)

PROBE 1542: 5'-AACTAAGAACGGCCATGCAC-CACCAT-3' (SEQ ID NO: 6)

PROBE 1545: 5'-TGGTGCCCTTCCGTCAATTTCTT-TAAGTTTCAGCCTTGCG-3' (SEQ ID NO: 7)

PROBE 1814: 5'-TCGCTGGCGCAAGGCCATG-CGATTCGAGAGGTTATTATGAATCAT-CAG-3' (SEQ ID NO: 8)

PROBE 1816: 5'-CAAGCTGATGACTTGTGCT-TACTAGGGATT-3' (SEQ ID NO: 9)

PROBE 1857: 5'-TCGGCATAGTTTGTGGT-TAAGACTACGACGGTATCTT-3' (SEQ ID NO: 10)

PROBE 1813: 5'-AAATGCTTTCGCAG-TAGTTGGTCTT-3' (SEQ ID NO: 11)

PROBE 1860: 5'-AAATGCTTTCGCAG-TAGTTGGTCTTCGGTAAATCCAAGAATTT-CACCTT-3' (SEQ ID NO: 12)

PROBE 1812: 5'-ACGTCCTATTTTATTATT-CCATGCTAAT-3' (SEQ ID NO: 13)

PROBE 1858: 5'-AAGTCATATTTCATTATT-CCATGCTAACT-3' (SEQ ID NO: 14)

PROBE 1859: 5'-TCGTCGAGTTATGTTATT-CCATGCAAAT-3' (SEQ ID NO: 15)

The specific behaviors of the aforementioned probes are dependent to a significant extent on the assay format in which they are employed. Conversely, the assay format will dictate certain of the optimal features of particular probes. The "essence" of the probes of the invention is not to be construed as restricted to the specific string of nucleotides in the named probes. For example, the length of these particular oligonucleotides was optimized for use in the dot blot assay (and certain other anticipated assays) described below. It is well known to those skilled in the art that optimal probe length will be a function of the stringency of the hybridization conditions chosen and hence the length of the instant probes may be altered accordingly. Also, in considering sets comprised of more than one probe, it is desirable that all probes behave in a compatible manner in any particular format in which they are employed. Thus, the exact length of a particular probe will to a certain extent, reflect its specific intended use.

The probes of the present invention are useful as oligonucleotide probes and can also be incorporated into larger polynucleotides of either ribonucleic acid or deoxyribonucleic acid. Sequences complementary to the probes described herein can be used as probes to rRNA genes. The preferred probes or their complements also can be employed as chain elongation initiators for polymerase chain reaction, sequencing or other applications.

Two additional preferred probes useful in this regard comprise:

Probe/Primer 936: 5'-(CCGAATTCGT-CGACAAC)CTGGTTGATCCTGCCAGT-3' (SEQ ID NO: 16)

Probe/Primer 935: 5'-(CCCGGGATCCAAGCT)T-GATCCTTCTGCAGGTTCACCTAC-3' (SEQ ID NO: 17)

Probe/Primer 936 is designed to hybridize to the 18S rDNA gene strand complementary to fungal 18S rRNA. Oligonucleotides 935 and 936 are designed for and most preferred for use in assays employing amplification, by the polymerase chain reaction method, of almost the entire 18S rRNA gene (rDNA) of fungi and relatives. The target specific "essence" of these two probe/primers resides in the portions of these oligonucleotides not included within the parenthesis. The nucleotides within the parentheses are preferably included since they add useful restriction endonuclease recognition (cloning) sites to the amplified products.

Probe Behavior During Hybridization

The experimental specificity of the preferred probes, as further documented in Example 1 and Tables 1, 2, and 3, may be summarized as follows:

Probe 1417: 100%; Inclusive for tested fungi, with negligible cross-reactivity to human RNA at 60° C. At 65° C. (hybridization temperature) signal is decreased for 2 of the 171 fungi, all others still strongly hybridize, and the human cross-reactivity is removed. Strong hybridization to wheat rRNA is evident.

Probe 1418: 100% inclusive for all tested fungi, with no cross-reactivity to human RNA.

Probe 1417: Is a subsequence of 1418, that is, it is a shorter version of the same probe.

Probe 1415: Inclusive for a subset of fungi, not including any Candida yeasts, but including the important pathogenic yeast, Cryptococcus.

Probe 1416: Inclusive of all of the tested strains from the genus Candida (Torulopsis) except for the species *Yarrowia (Candida) lipolytica*. Also inclusive for Hansenula, Metschnikowia, and Saccharomyces—all close evolutionary relatives of Candida yeasts. One Penicillium species yields a weak signal with this probe in this assay format.

Probe IG707: 100% inclusive for *Yarrowia lipolytica*. Combined with probe 1416, these two are fully inclusive for the Candidas tested.

Probes 1415, 1416, and IG707: are homologous, that is, they all hybridize to the same region of the 18S rRNA.

Probe 1542: 100% inclusive for all tested fungi plus human RNA. Designed as a companion probe for 1417 or 1418 in a dual probe (sandwich type) hybridization scheme.

Probe 1545: 100% inclusive for all tested fungi plus human RNA. Designed as a companion probe for 1417 or 1418 in a dual probe (sandwich type) hybridization scheme.

Probe 1814: Broadly fungal inclusive, particularly under 50° C. hybridization conditions.

Probe 1816: Broadly fungal inclusive at 50° C.

Probe 1857: Broadly inclusive with slight hybridization to non-fungi at 50° C.

Probe 1813: Broadly inclusive at 50° C.

Probe 1860: Broadly inclusive at 50° C. or 60° C. hybridization.

Probe 1813: Is a subsequence of Probe 1860.

Probe 1812. Very broadly inclusive at 50° C. with no cross-reactivity to human or wheat germ RNA.

Probe 1858: Designed to hybridize to Zygomycetes, and thus complements the hybridizing behavior of Probe 1812.

Probe 1859: Designed to hybridize to *Yarrowia lipolytica*, and thus complements the hybridizing behavior of Probe 1812.

Probes 1812, 1858, and 1859: Are a homologous set—that is they all hybridize to an identical location on the 18S rRNA molecule. As a set, they fail to hybridize strongly to only two strains (see Tables 2 and 3).

Non-homologous probes, such as Probes 1857 and 1860 are designed to be used together in dual probe ,says as described in example 2.

Probe/primers 935 and 936 have been used to amplify 18S rDNA from all fungal taxa tested, including Aspergillus, Candida, Penicillium, Cryptococcus, and Blastomyces.

EXAMPLE 1

Dot-Blot Analysis of Probe Hybridization Behavior

Dot-blot analysis, in accordance with well known procedures, involves immobilizing a nucleic acid or a population of nucleic acids on a filter such as nitrocellulose, nylon, or other derivatized membranes which can readily be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target will exhibit a higher level of hybridization than probes containing less complementarity.

Probes of the present invention were tested in a dot-blot format. One hundred nanograms of target RNA, purified by phenol extraction and centrifugation through cesium trifluoroacetate gradients, was denatured and spotted on a nylon membrane. Probes were isotopically labelled with the addition of a 32-Phosphorous moiety to the 5' end of the oligonucleotide. Hybridization of probes occurred, at temperatures indicated, in the presence of 1.08 M sodium chloride, 60 mM sodium phosphate, and 6 mM ethylenediamine tetraacetic acid, pH 7.4. Unhybridized probe was removed by washing at a salt concentration one-third of the hybridization condition. The filters were exposed to X-ray film and the intensity of hybridization signals was evaluated after three hours of exposure.

Tables 1, 2, and 3 summarize the behavior of the probes as tested by the above procedure and documents the specificity summarized above.

EXAMPLE 2

Dual Probe Hybridization

In actual practice, many applications of these probes would employ a pair of probes being used simultaneously in a "sandwich" hybridization scheme of "capture" probe and "detector" probe as shown in the FIGURE. The capture probe[12] ideally would be a bifunctional polynucleotide manufactured by adding a homopolymeric 3' tail to a probe with high target specificity. The tail would, in turn hybridize to the complementary homopolymer[11] on a solid surface[10], such as a glass bead or a filter disc. Hybridization of the capture probe[12] to its target[15], in this case Fungal spirochete 18S rRNA, would complex the target[15] with the solid support[10]. The detector probe[13], advantageously also with some degree of specificity, would be part of a preferred detection scheme relying on radioactivity, fluorescence, chemiluminescence, color, etc. (detection moiety[14]) which would report the presence of the entire hybridization complex.

EXAMPLE 3

Clinical Diagnosis of Fungal Septicemia from Blood, Sputum, or Cerebrospinal Fluid Sample The clinical sample is ideally processed so as to liberate the total nucleic acid content such as by sonication, vortexing with glass beads, detergent lysis using an agent such as SDS or by chemical treatment. Alternatively, fungal cells may be partially purified by, for example, the DuPont Isolator System, followed by cell lysis. The sample, containing disrupted fungi is then incubated in the presence of capture probe, detector probe, and ideally magnetic particle beads which have been derivatized with oligo-Thymidine (see also Example 2) in a chaotropic buffer such as guanidinium isothiocyanate described by Gillespie et al U.S. Ser. No. 299,150.

If yeast or mold 18S rRNA target molecules are present, a Bead+Capture Probe+Target+Detector Probe hybridization complex is formed. The exterior presence of a magnet near the bottom of the reaction tube will cause the magnetic particle—hybridization complex to adhere to the interior side of the tube thereby advantageously enabling removal of the unreacted components such as sample matrix, unbound probe, etc. Repeated rehydration and denaturation of the bead-probe-target complex would enable significant background reduction (as more fully described in Collins et al, U.S. Ser. No. 922,155, EPA 87309308.2 and U.S. Ser. No. 136,920, EPA 88312135.2). In this example, final detection could entail spotting the beads on membrane and assaying by autoradiography.

For such assays, the following capture and detector probe combinations are examples of the preferred pairs:

Probes 1417+1542, Probes 1417+1545, Probes 1418+1542,
Probes 1418+1545, Probes 1416+1812, Probes 1812+1860,
Probes 1857+1860.

EXAMPLE 4

Clinical Diagnosis of Fungal Infection from Human Sample Employing Polymerase Chain Reaction Amplification of Fungal rDNA Sample processing such as provided in Example 3 is ideally designed so as to yield DNA. The DNA is further treated to make it single stranded (e.g. by melting) in preparation for polymerase chain reaction ("PCR") amplification. Probe/Primer 936 and Probe/Primer 935 are ideally employed in conjunction with the clinical sample in the standard PCR procedures. Resultant material may then be suitably assayed utilizing the "sandwich" hybridization procedures of Example 2 with any of the probes described herein. The polymerase chain reaction can, itself, be made highly specific by employing Probe/Primer 936 in conjunction with, for example, Probe 1812. Detection is advantageously accomplished using Probe 1814 for capture and Probes 1415 and 1416 for detection.

EXAMPLE 5

In situ Hybridization as a Cytological Stain

The probes of the present invention can also be advantageously employed as cytological staining reagents. For example, a sputum sample is applied to a microscope slide. After appropriate fixation and lysis, hybridization with the probes of the present invention is carried out in situ. In this manner, fungi could be visualized in a specimen by fluorescently labelling Probe 1416 and examining the slide using a fluorescent microscope.

EXAMPLE 6

Confirmation of Fungemia Following Culture

Following a standard cultivation step utilizing the Bartec, Roche Septi-Chek, or DuPont Isolator, a colony or liquid culture is tested for fungal presence employing Probes 1418 and 1542 in the procedures described in Example 2. Of good advantage is that pure culture is not necessary.

It will be readily appreciated by those skilled in the art that various modifications to the procedures or probes set forth herein may be made without departing from either the spirit or scope of the present invention. In particular, when modifications of the probes,such as by deleting one or two end nucleotides with accompanying adjustments in hybridization conditions are to be deemed equivalent.

TABLE 1

DOTBLOT HYBRIDIZATION DATA

| NAME/STRAIN | | 1417 60 deg C. | 1417 65 deg C. | 1418 65 deg C. | 1415 65 deg C. | 1416 65 deg C. | IG707 65 deg C. | 1542 60 deg C. | 1545 60 deg C. |
|---|---|---|---|---|---|---|---|---|---|
| *Alternaria alternata* | 13963 | + | + | + | − | − | − | + | + |
| *Agaricus brunnescens* | n5829 | + | + | + | + | − | − | + | + |
| *Aspergillus flavus* | 10124 | + | + | + | +− | − | − | + | + |
| *Aspergillus fumigatus* | 36607 | + | + | + | +− | − | − | + | + |
| *Aspergillus nidulans* | 10074 | + | + | + | − | − | − | + | + |
| *Aspergillus niger* | 16888 | + | + | + | +− | − | − | + | + |
| *Aspergillus parasiticus* | 15517 | + | + | + | +− | − | − | + | + |
| *Aspergillus terreus* | 46941 | + | + | + | +− | − | − | + | + |
| *Aspergillus versicolor* | 95776 | + | + | + | +−− | − | − | + | + |
| *Blastomyces dermatitidis* | 60916 | + | + | + | +− | − | − | + | + |
| *Byssochlamys fulva* | 10099 | + | + | + | − | − | − | + | + |
| *Candida albicans* | 11006 | + | + | + | − | + | − | + | + |
| *Candida albicans* | 14053 | + | + | + | − | + | − | + | + |
| *Candida albicans* | 18804 | + | + | + | − | + | − | + | + |
| *Candida albicans* | 24433 | + | + | + | − | + | − | + | + |
| *Candida albicans* | 36252 | + | + | + | − | + | − | + | + |

TABLE 1-continued

DOTBLOT HYBRIDIZATION DATA

| NAME/STRAIN | | PROBE | | | | | | | |
|---|---|---|---|---|---|---|---|---|---|
| | | 1417 60 deg C. | 1417 65 deg C. | 1418 65 deg C. | 1415 65 deg C. | 1416 65 deg C. | IG707 65 deg C. | 1542 60 deg C. | 1545 60 deg C. |
| Candida albicans | 60193 | + | + | + | − | + | − | + | + |
| Candida guilliermondii | 6260 | + | + | + | − | + | − | + | + |
| Candida kefyr | 4135 | + | + | + | − | + | − | + | + |
| Candida kefyr | 46764 | + | + | + | − | + | − | + | + |
| Candida krusei | 6258 | + | + | + | − | + | − | + | + |
| Candida lusitaniae | 42720 | + | + | + | − | + | − | + | + |
| Candida parapsilosis | 22019 | + | + | + | − | + | − | + | + |
| Candida rugosa | 58964 | + | + | + | − | + | − | + | + |
| Candida tropicalis | 750 | + | + | + | − | + | − | + | + |
| Candida tropicalis | 13803 | + | + | + | − | + | − | + | + |
| Candida tropicalis | 42678 | + | + | + | − | + | − | + | + |
| Candida utilis | 9226 | + | + | + | − | + | − | + | + |
| Candida viswanathii | 22981 | + | + | + | − | + | − | + | + |
| Chrysosporium keratinophilum | 14803 | + | + | + | + | − | − | + | + |
| Cladosporium castellani | 24788 | + | + | + | + | − | − | + | + |
| Cryptococcus neoformans | 14116 | + | + | + | + | − | − | + | + |
| Cryptococcus neoformans | 32045 | + | + | + | + | − | − | + | + |
| Cyathus stercoreus | n6473 | + | + | + | − | − | − | + | + |
| Entomophthora virulenta | 14207 | + | +−− | + | − | − | − | + | + |
| Epidermophyton floccosum | 52066 | + | + | + | + | − | − | + | + |
| Filobasidiella neoformans | 6352 | + | + | + | + | − | − | + | + |
| Fusarium oxysporum | 16322 | + | + | + | +− | − | − | + | + |
| Hansenula polymorpha | 34438 | + | + | + | − | + | − | + | + |
| Histoplasma capsulatum | 12700 | + | + | + | +− | − | − | + | + |
| Geotrichum candidum | 34614 | + | + | + | − | − | − | + | + |
| Lipomyces starkeyi | n11557 | + | + | + | − | − | − | + | + |
| Metschnikowia bicuspidata | 22297 | + | + | + | − | + | − | + | + |
| Microsporum racemosum | 38556 | + | + | + | +−− | − | − | + | + |
| Morchella crassipes | 18408 | + | + | + | nt | nt | nt | nt | nt |
| Mucor rouxii | 24905 | + | + | + | + | − | − | + | + |
| Neurospora crassa | 14692 | + | + | + | + | − | − | + | + |
| Neurospora sitophila | 36935 | + | + | + | + | − | − | + | + |
| Paracoccidioides brasiliensis | 48093 | + | + | + | − | − | − | + | + |
| Penicillium chrysogenum | 10106 | + | + | + | − | − | − | + | + |
| Penicillium digitatum | 48113 | + | + | + | − | − | − | + | + |
| Penicillium notatum | 9179 | + | + | + | − | +− | − | + | + |
| Phycomyces blakesleeanus | n1464 | + | + | + | + | − | − | + | + |
| Pityrosporum ovale | 14521 | + | + | + | + | − | − | + | + |
| Pseudallescheria boydii | 28169 | + | + | + | + | − | − | + | + |
| Rhizopus oligosporus | 22959 | + | + | + | + | − | − | + | + |
| Rhodosporidium toruloides | 10788 | + | + | + | + | − | − | + | + |
| Rhodotorula rubra | 9449 | + | + | + | + | − | − | + | + |
| Saccaromyces cerevisiae | 18824 | + | + | + | − | + | − | + | + |
| Saccharomycodes ludwigii | n12792 | + | + | + | − | − | − | + | + |
| Schizosaccharomyces octosporus | 4206 | + | + | + | − | − | − | + | + |
| Sporothrix schenkii | 14284 | + | + | + | − | − | − | + | + |
| Taphrina deformans | nT857 | + | + | + | − | − | − | + | + |
| Torulopsis glabrata | 2001 | + | + | + | − | + | − | + | + |
| Tremella mesenterica | 42219 | + | + | + | − | − | − | + | + |
| Trichophyton mentagrophytes | 28185 | + | + | + | − | − | − | + | + |
| Trichophyton rubrum | 28188 | + | + | + | − | − | − | + | + |
| Trichosporon beigelii | 28592 | + | + | + | + | − | − | + | + |
| Trichosporon capitatum | 10663 | + | + | + | − | − | − | + | + |
| Ustilago maydis | j1402 | + | +− | + | + | − | − | + | + |
| Verticillium dahliae | 16535 | + | + | + | + | − | − | + | + |
| Yarrowia lipolytica | 18942 | + | + | + | − | − | + | + | + |
| EXCLUSIVITY | | | | | | | | | |
| HUMAN/CaSKi | | − | − | − | − | − | − | + | + |
| Staphylococcus aureus | GT2047 | − | − | − | − | − | − | − | − |
| Escherichia coli | 12036 | − | − | − | − | − | − | − | − |
| Stool RNA | | − | nt | − | − | − | − | − | +− |
| Wheat germ RNA | | + | nt | + | − | − | − | + | + |
| Candida albicans | | | | | | | | | |
| 151-87 | | + | + | + | − | + | − | + | + |
| 184-87 | | + | + | + | − | + | − | + | + |
| 192-87 | | + | + | + | − | + | − | + | + |
| 738-88 | | + | + | + | − | + | − | + | + |
| 784-88 | | + | + | + | − | + | − | + | + |
| 819-88 | | + | + | + | − | + | − | + | + |
| 854-88 | | + | + | + | − | + | − | + | + |
| 864-88 | | + | + | + | − | + | − | + | + |
| 875-88 | | + | + | + | − | + | − | + | + |
| 876-88 | | + | + | + | − | + | − | + | + |
| 889-88 | | + | + | + | − | + | − | + | + |
| 892-88 | | + | + | + | − | + | − | + | + |
| 896-88 | | + | + | + | − | + | − | + | + |
| 901-88 | | + | + | + | − | + | − | + | + |

TABLE 1-continued

DOTBLOT HYBRIDIZATION DATA

| NAME/STRAIN | PROBE | | | | | | | |
|---|---|---|---|---|---|---|---|---|
| | 1417 60 deg C. | 1417 65 deg C. | 1418 65 deg C. | 1415 65 deg C. | 1416 65 deg C. | IG707 65 deg C. | 1542 60 deg C. | 1545 60 deg C. |
| 903-88 | + | + | + | − | + | − | + | + |
| 904-88 | + | + | + | − | + | − | + | + |
| 917-88 | + | + | + | − | + | − | + | + |
| 921-88 | + | + | + | − | + | − | + | + |
| 925-88 | + | + | + | − | + | − | + | + |
| 926-88 | + | + | + | − | + | − | + | + |
| 939-88 | + | + | + | − | + | − | + | + |
| 943-88 | + | + | + | − | + | − | + | + |
| 946-88 | + | + | + | − | + | − | + | + |
| 966-88 | + | + | + | − | + | − | + | + |
| 993-88 | + | + | + | − | + | − | + | + |
| 161-87 | + | + | + | − | + | − | + | + |
| 162-87 | + | + | + | − | + | − | + | + |
| 190-87 | + | + | + | − | + | − | + | + |
| 203-87 | + | + | + | − | + | − | + | + |
| 207-87 | + | + | + | − | + | − | + | + |
| 223-87 | + | + | + | − | + | − | + | + |
| 227-87 | + | + | + | − | + | − | + | + |
| 258-87 | + | + | + | − | + | − | + | + |
| 262-87 | + | + | + | − | + | − | + | + |
| 266-87 | + | + | + | − | + | − | + | + |
| 291-87 | + | + | + | − | + | − | + | + |
| 296-87 | + | + | + | − | + | − | + | + |
| 307-87 | + | + | + | − | + | − | + | + |
| 308-87 | + | + | + | − | + | − | + | + |
| 326-87 | + | + | + | − | + | − | + | + |
| 342-87 | + | + | + | − | + | − | + | + |
| 662-87 | + | + | + | − | + | − | + | + |
| 996-87 | + | + | + | − | + | − | + | + |
| 984-88 | + | + | + | − | + | − | + | + |
| 100888 | + | + | + | − | + | − | + | + |
| 101888 | + | + | + | − | + | − | + | + |
| *Candida guilliermondii* | | | | | | | | |
| 105586 | + | + | + | − | + | − | + | + |
| 350-87 | + | + | + | − | + | − | + | + |
| 715-88 | + | + | + | − | + | − | + | + |
| 974-88 | + | + | + | − | + | − | + | + |
| *Candida krusei* | | | | | | | | |
| 46-87 | + | + | + | − | + | − | + | + |
| 528-87 | + | + | + | − | + | − | + | + |
| 842-88 | + | + | + | − | + | − | + | + |
| 939-88 | + | + | + | − | + | − | + | + |
| *Candida (Yarrowia) lipolytica* | | | | | | | | |
| 056584 | + | + | + | − | − | + | + | + |
| 103486 | + | + | + | +− | − | + | + | + |
| 125085 | + | + | + | − | − | + | + | + |
| 453-87 | + | + | + | − | − | + | + | + |
| *Candida lusitaniae* | | | | | | | | |
| 121585 | + | + | + | − | + | − | + | + |
| 121685 | + | + | + | − | + | − | + | + |
| 403-87 | + | + | + | − | + | − | + | + |
| 964-88 | + | + | + | − | + | − | + | + |
| *Candida parapsilosis* | | | | | | | | |
| 175-87 | + | + | + | − | + | − | + | + |
| 176-87 | + | + | + | − | + | − | + | + |
| 491-87 | + | + | + | − | + | − | + | + |
| 492-87 | + | + | + | − | + | − | + | + |
| 746-88 | + | + | + | − | + | − | + | + |
| 754-88 | + | + | + | − | + | − | + | + |
| 828-88 | + | + | + | − | + | − | + | + |
| 951-88 | + | + | + | − | + | − | + | + |
| *Candida (kefyr) pseudotropicalis* | | | | | | | | |
| 091486 | + | + | + | − | + | − | + | + |
| 100188 | + | + | + | − | + | − | + | + |
| 102886 | + | + | + | − | + | − | + | + |
| 999-88 | + | + | + | − | + | − | + | + |
| *Candida tropicalis* | | | | | | | | |
| 484-87 | + | + | + | − | + | − | + | + |
| 784-88 | + | + | + | − | + | − | + | + |
| 802-88 | + | + | + | − | + | − | + | + |
| 846-88 | + | + | + | − | + | − | + | + |
| 997-88 | + | + | + | − | + | − | + | + |
| 999-88 | + | + | + | − | + | − | + | + |
| 150-87 | + | + | + | − | + | − | + | + |
| 210-87 | + | + | + | − | + | − | + | + |
| 224-87 | + | + | + | − | + | − | + | + |

TABLE 1-continued

DOTBLOT HYBRIDIZATION DATA

| NAME/STRAIN | PROBE | | | | | | | |
|---|---|---|---|---|---|---|---|---|
| | 1417 60 deg C. | 1417 65 deg C. | 1418 65 deg C. | 1415 65 deg C. | 1416 65 deg C. | IG707 65 deg C. | 1542 60 deg C. | 1545 60 deg C. |
| 319-87 | + | + | + | − | + | − | + | + |
| 573-87 | + | + | + | − | + | − | + | + |
| *Torulopsis glabrata* | | | | | | | | |
| 233-87 | + | + | + | − | + | − | + | + |
| 260-87 | + | + | + | − | + | − | + | + |
| 275-87 | + | + | + | − | + | − | + | + |
| 288-87 | + | + | + | − | + | − | + | + |
| 334-87 | + | + | + | − | + | − | + | + |
| 359-87 | + | + | + | − | + | − | + | + |
| 373-87 | + | + | + | − | + | − | + | + |
| 506-87 | + | + | + | − | + | − | + | + |
| 562-87 | + | + | + | − | + | − | + | + |
| 573-87 | + | + | + | − | + | − | + | + |
| 701-87 | + | + | + | − | + | − | + | + |
| 901-88 | + | + | + | − | + | − | + | + |
| 903-88 | + | + | + | − | + | − | + | + |
| *Cryptococcus albidus* | | | | | | | | |
| 83-0085 | + | nt | + | nt | nt | nt | nt | nt |
| 85-0707 | + | nt | + | nt | nt | nt | nt | nt |
| 85-0808 | + | nt | + | nt | nt | nt | nt | nt |
| 85-1452 | + | nt | + | nt | nt | nt | nt | nt |
| 88-1047 | + | nt | + | nt | nt | nt | nt | nt |
| *Cryptococcus laurentii* | | | | | | | | |
| 82-0600 | + | nt | + | nt | nt | nt | nt | nt |
| 87-0657 | + | nt | + | nt | nt | nt | nt | nt |
| 88-0010 | + | nt | + | nt | nt | nt | nt | nt |
| *Cryptococcus neoformans* A | | | | | | | | |
| 151 | + | nt | + | nt | nt | nt | nt | nt |
| 159 | + | nt | + | nt | nt | nt | nt | nt |
| 160 | + | nt | + | nt | nt | nt | nt | nt |
| 161 | + | nt | + | nt | nt | nt | nt | nt |
| *Cryptococcus neoformans* B | | | | | | | | |
| 182 | + | nt | + | nt | nt | nt | nt | nt |
| 184 | + | nt | + | nt | nt | nt | nt | nt |
| B3174a | + | nt | + | nt | nt | nt | nt | nt |
| B3268b | + | nt | + | nt | nt | nt | nt | nt |
| B3271a | + | nt | + | nt | nt | nt | nt | nt |
| *Cryptococcus neoformans* C | | | | | | | | |
| 298 | + | nt | + | nt | nt | nt | nt | nt |
| B3185a | + | nt | + | nt | nt | nt | nt | nt |
| B3186a | + | nt | + | nt | nt | nt | nt | nt |
| B3267b | + | nt | + | nt | nt | nt | nt | nt |
| CP110 | + | nt | + | nt | nt | nt | nt | nt |
| *Cryptococcus neoformans* D | | | | | | | | |
| 151 | + | nt | + | nt | nt | nt | nt | nt |
| 165C | + | nt | + | nt | nt | nt | nt | nt |
| 166 | + | nt | + | nt | nt | nt | nt | nt |
| 167 | + | nt | + | nt | nt | nt | nt | nt |
| 168 | + | nt | + | nt | nt | nt | nt | nt |

TABLE 2

DOTBLOT HYBRIDIZATION DATA

| NAME/STRAIN | | PROBE | | | | | | | |
|---|---|---|---|---|---|---|---|---|---|
| | | 1859 50 deg C. | 1859 60 deg C. | 1860 50 deg C. | 1860 60 deg C. | 1858 50 deg C. | 1858 60 deg C. | 1857 50 deg C. | 1857 60 deg C. |
| *Alternaria alternata* | 13963 | − | − | + | + | − | − | + | + |
| *Agaricus brunnescens* | n5829 | − | − | + | + | − | − | + | +−− |
| *Aspergillus flavus* | 10124 | − | − | + | + | − | − | + | + |
| *Aspergillus fumigatus* | 36607 | − | − | + | + | − | − | + | + |
| *Aspergillus nidulans* | 10074 | − | − | + | + | − | − | + | + |
| *Aspergillus niger* | 16888 | − | − | + | + | − | − | + | + |
| *Aspergillus parasiticus* | 15517 | − | − | + | + | − | − | + | + |
| *Aspergillus terreus* | 46941 | − | − | + | + | − | − | + | + |
| *Aspergillus versicolor* | 95776 | − | − | + | + | − | − | + | + |
| *Blastomyces dermatitidis* | 60916 | − | − | + | + | − | − | + | + |
| *Byssochlamys fulva* | 10099 | − | − | + | + | − | − | + | + |
| *Candida albicans* | 11006 | − | − | + | + | − | − | + | + |
| *Candida albicans* | 14053 | − | − | + | + | − | − | + | + |
| *Candida albicans* | 18804 | − | − | + | + | − | − | + | + |
| *Candida albicans* | 24433 | − | − | + | + | − | − | + | + |
| *Candida albicans* | 36252 | − | − | + | + | − | − | + | + |
| *Candida albicans* | 60193 | − | − | + | + | − | − | + | + |
| *Candida guilliermondii* | 6260 | − | − | + | + | − | − | + | + |

TABLE 2-continued

DOTBLOT HYBRIDIZATION DATA

| NAME/STRAIN | | 1859 50 deg C. | 1859 60 deg C. | 1860 50 deg C. | 1860 60 deg C. | 1858 50 deg C. | 1858 60 deg C. | 1857 50 deg C. | 1857 60 deg C. |
|---|---|---|---|---|---|---|---|---|---|
| *Candida kefyr* | 4135 | − | − | + | + | +− | − | + | + |
| *Candida kefyr* | 46764 | − | − | + | + | +− | − | + | + |
| *Candida krusei* | 6258 | − | − | + | + | − | − | + | + |
| *Candida lusitaniae* | 42720 | − | − | + | + | − | − | + | + |
| *Candida parapsilosis* | 22019 | − | − | + | + | − | − | + | + |
| *Candida rugosa* | 58964 | − | − | + | + | − | − | +− | +−− |
| *Candida tropicalis* | 750 | − | − | + | + | − | − | + | + |
| *Candida tropicalis* | 13803 | − | − | + | + | − | − | + | + |
| *Candida tropicalis* | 42678 | − | − | + | + | − | − | + | + |
| *Candida utilis* | 9226 | − | − | + | + | − | − | + | + |
| *Candida viswanathii* | 22981 | − | − | + | + | − | − | + | + |
| *Chrysosporium keratinophilum* | 14803 | − | − | + | + | − | − | + | + |
| *Cladosporium castellani* | 24788 | +−− | − | + | + | +−− | − | + | +− |
| *Cryptococcus neoformans* | 14116 | − | − | + | + | − | − | +− | − |
| *Cryptococcus neoformans* | 32045 | − | − | + | + | − | − | +− | − |
| *Cyathus stercoreus* | n6473 | − | − | + | + | − | − | + | +−− |
| *Entomophthora virulenta* | 14207 | − | − | + | +− | − | − | + | + |
| *Epidermophyton floccosum* | 52066 | − | − | + | + | − | − | + | +− |
| *Filobasidiella neoformans* | 6352 | − | − | + | + | − | − | +− | + |
| *Fusarium oxysporum* | 16322 | − | − | + | + | +−− | − | + | − |
| *Hansenula polymorpha* | 34438 | − | − | + | + | − | − | + | + |
| *Histoplasma capsulatum* | 12700 | − | − | + | + | − | − | + | + |
| *Geotrichum candidum* | 34614 | − | − | + | + | − | − | + | + |
| *Lipomyces starkeyi* | n11557 | − | − | + | + | − | − | + | + |
| *Metschnikowia bicuspidata* | 22297 | − | − | + | + | − | − | + | + |
| *Microsporum racemosum* | 38556 | − | − | + | + | − | − | + | + |
| *Mucor rouxii* | 24905 | +−− | − | + | + | + | +−− | + | + |
| *Neurospora crassa* | 14692 | − | − | + | + | − | − | + | + |
| *Neurospora sitophila* | 36935 | − | − | + | + | − | − | + | + |
| *Paracoccidioides brasiliensis* | 48093 | − | − | + | + | − | − | + | + |
| *Penicillium chrysogenum* | 10106 | − | − | + | + | − | − | + | + |
| *Penicillium digitatum* | 48113 | − | − | + | + | − | − | + | + |
| *Penicillium notatum* | 9179 | − | − | + | + | − | − | + | + |
| *Phycomyces blakesleeanus* | n1464 | − | − | + | + | + | +−− | + | + |
| *Pityrosporum ovale* | 14521 | − | − | + | + | − | − | + | +−− |
| *Pseudallescheria boydii* | 28169 | − | − | + | + | − | − | + | + |
| *Rhizopus oligosporus* | 22959 | +−− | − | + | + | + | +−− | + | + |
| *Rhodosporidium toruloides* | 10788 | − | − | + | + | − | − | +−− | − |
| *Rhodotorula rubra* | 9449 | − | − | + | + | − | − | +−− | − |
| *Saccharomyces cerevisiae* | 18824 | − | − | + | + | − | − | + | + |
| *Saccharomycodes ludwigii* | n12792 | − | − | + | + | − | − | + | + |
| *Schizosaccharomyces octosporus* | 4206 | − | − | + | + | − | − | + | + |
| *Sporothrix schenkii* | 14284 | − | − | + | + | − | − | + | + |
| *Taphrina deformans* | nT857 | − | − | + | + | − | − | + | + |
| *Torulopsis glabrata* | 2001 | − | − | + | + | +− | − | + | + |
| *Tremella mesenterica* | 42219 | − | − | + | +−− | − | − | + | +−− |
| *Trichophyton mentagrophytes* | 28185 | − | − | + | + | − | − | + | + |
| *Trichophyton rubrum* | 28188 | − | − | + | + | − | − | + | + |
| *Trichosporon beigelii* | 28592 | − | − | + | +− | − | − | + | +−− |
| *Trichosporon capitatum* | 10663 | − | − | +− | − | − | − | + | + |
| *Ustilago maydis* | j1402 | − | − | + | +−− | − | · | + | +−− |
| *Verticillium dahliae* | 16535 | − | − | + | + | − | − | + | + |
| *Yarrowia lipolytica* | 18942 | + | +−− | + | + | − | − | + | + |
| EXCLUSIVITY | | | | | | | | | |
| HUMAN/CaSKi | | − | − | +−− | − | − | − | +−− | − |
| *Staphylococcus aureus* | GT204 | − | − | − | − | − | − | − | − |
| *Escherichia coli* | 12036 | − | − | − | − | − | − | − | − |
| Stool RNA | | − | − | − | − | − | − | − | − |
| Wheat germ RNA | | − | − | +− | +− | − | − | +−− | − |
| *Candida albicans* | | | | | | | | | |
| 190-87 | | − | − | + | + | − | − | + | + |
| 266-87 | | − | − | + | + | − | − | + | + |
| *Candida guilliermondii* | | | | | | | | | |
| 350-87 | | − | − | + | +− | − | − | + | + |
| 715-88 | | − | − | + | + | − | − | + | + |
| *Candida krusei* | | | | | | | | | |
| 842-88 | | − | − | + | + | − | − | + | + |
| 939-88 | | − | − | + | + | − | − | + | + |
| *Candida (Yarrowia) lipolytica* | | | | | | | | | |
| 056584 | | + | +−− | + | + | − | − | + | + |
| 125085 | | + | +−− | + | + | − | − | + | + |
| *Candida lusitaniae* | | | | | | | | | |
| 121585 | | − | − | + | + | − | − | + | + |
| 121685 | | − | − | + | + | − | − | + | + |
| *Candida parapsilosis* | | | | | | | | | |
| 176-87 | | − | − | + | + | − | − | + | + |

TABLE 2-continued

DOTBLOT HYBRIDIZATION DATA

| NAME/STRAIN | | 1859 50 deg C. | 1859 60 deg C. | 1860 50 deg C. | 1860 60 deg C. | 1858 50 deg C. | 1858 60 deg C. | 1857 50 deg C. | 1857 60 deg C. |
|---|---|---|---|---|---|---|---|---|---|
| 754-88 | | − | − | + | + | − | − | + | + |
| *Candida (kefyr) pseudotropicalis* | | | | | | | | | |
| 100188 | | − | − | + | + | + | − | + | + |
| 999-88 | | − | − | + | + | + | − | + | + |
| *Candida tropicalis* | | | | | | | | | |
| 150-87 | | − | − | + | + | − | − | + | + |
| 210-87 | | − | − | + | + | − | − | + | + |
| *Torulopsis glabrata* | | | | | | | | | |
| 288-87 | | − | − | + | + | + | − | + | + |
| 334-87 | | − | − | + | + | + | − | + | + |
| *Cryptococcus albidus* | | | | | | | | | |
| 83-0085 | | − | − | + | +− | − | − | +− | − |
| 85-0707 | | − | − | + | + | − | − | +− | − |
| *Cryptococcus laurentii* | | | | | | | | | |
| 82-0600 | | − | − | +− | +−− | − | − | +− | +−− |
| 87-0657 | | − | − | +− | +−− | − | − | +− | +−− |
| *Cryptococcus neoformans* A | | | | | | | | | |
| 151 | | − | − | +− | +− | − | − | +− | − |
| 162 | | − | − | +− | +− | − | − | +− | − |
| *Cryptococcus neoformans* B | | | | | | | | | |
| 184 | | − | − | +− | +− | − | − | +− | − |
| B3174a | | − | − | +− | +−. | − | − | +− | − |
| *Cryptococcus neoformans* C | | | | | | | | | |
| 298 | | − | − | +− | +− | − | − | +− | − |
| B3185a | | − | − | +− | +− | − | − | +− | − |
| *Cryptococcus neoformans* D | | | | | | | | | |
| 161 | | − | − | +− | +− | − | − | +− | − |
| 166 | | − | − | +− | +− | − | − | +− | − |
| ADDITIONAL ASPERGILLI AND PENICILLIUM | | | | | | | | | |
| *Aspergillus clavatus* | 9192 | − | − | + | + | − | − | + | + |
| *Aspergillus niger* | 10535 | − | − | + | + | − | − | + | + |
| *Aspergillus niger* | 16404 | − | − | + | + | − | − | + | + |
| *Aspergillus niger* | 16880 | − | − | + | + | − | − | + | + |
| *Aspergillus oryzae* | 14895 | − | − | + | + | − | − | + | + |
| *Aspergillus repens* | 48521 | − | − | + | + | − | − | + | + |
| *Penicillium chrysogenum* | 10002 | − | − | + | + | − | − | + | + |
| *Penicillium expasum* | 7861 | − | − | + | + | − | − | + | + |
| *Penicillium italicum* | 48114 | − | − | + | + | − | − | + | + |
| *Penicillium roquefortii* | 10110 | − | − | + | + | − | − | + | + |
| ADDITIONAL BLASTOMYCES AND HISTOPLASMAS | | | | | | | | | |
| *Blastomyces dermatitidis* | 064571 | − | − | + | + | − | − | + | + |
| *Blastomyces dermatitidis* | 82-0741 | − | − | + | + | − | − | + | + |
| *Blastomyces dermatitidis* | CDCB44 | − | − | +− | + | − | − | + | + |
| *Blastomyces dermatitidis* | NYS48 | − | − | + | + | − | − | + | + |
| *Histoplasma capsulatum* | CDCA28 | − | − | + | + | − | − | + | + |
| *Histoplasma capsulatum* | NYS211 | − | − | + | + | − | − | + | + |
| *Histoplasma capsulatum* | NYS214 | − | − | + | + | − | − | + | + |
| *Histoplasma capsulatum* | NYS215 | − | − | + | + | − | − | + | + |
| *Histoplasma capsulatum* | NYS216 | − | − | + | + | − | − | + | + |
| *Histoplasma capsulatum* | NYS232 | − | − | + | + | − | − | + | + |

TABLE 3

DOTBLOT HYBRIDIZATION DATA

| NAME/STRAIN | | 1813 50 deg C. | 1813 60 deg C. | 1814 50 deg C. | 1814 60 deg C. | 1812 50 deg C. | 1812 60 deg C. | 1816 50 deg C. | 1816 60 deg C. |
|---|---|---|---|---|---|---|---|---|---|
| *Alternaria alternata* | 13963 | + | − | +− | − | + | +−− | +− | − |
| *Agaricus brunnescens* | n5829 | + | +− | + | + | + | + | +− | − |
| *Aspergillus flavus* | 10124 | + | − | + | + | + | +−− | +− | − |
| *Aspergillus fumigatus* | 36607 | + | − | + | +− | + | +−− | +− | − |
| *Aspergillus nidulans* | 10074 | + | − | + | + | + | +−− | +− | − |
| *Aspergillus niger* | 16888 | + | − | + | +− | + | +−− | +− | − |
| *Aspergillus parasiticus* | 15517 | + | − | + | + | + | +−− | +− | − |
| *Aspergillus terreus* | 46941 | + | − | + | + | + | +−− | +− | − |
| *Aspergillus versicolor* | 95776 | + | − | + | +− | + | +−− | +− | − |
| *Blastomyces dermatitidis* | 60916 | + | − | + | + | + | +−− | + | − |
| *Byssochlamys fulva* | 10099 | + | − | + | + | + | +−− | +− | − |
| *Candida albicans* | 11006 | + | − | + | + | + | +−− | + | − |
| *Candida albicans* | 14053 | + | − | + | + | + | +−− | + | − |
| *Candida albicans* | 18804 | + | − | + | + | + | +−− | + | − |
| *Candida albicans* | 24433 | + | − | + | + | + | +−− | + | − |
| *Candida albicans* | 36252 | + | − | + | + | + | +−− | + | − |

TABLE 3-continued

DOTBLOT HYBRIDIZATION DATA

| NAME/STRAIN | | PROBE | | | | | | | |
|---|---|---|---|---|---|---|---|---|---|
| | | 1813 50 deg C. | 1813 60 deg C. | 1814 50 deg C. | 1814 60 deg C. | 1812 50 deg C. | 1812 60 deg C. | 1816 50 deg C. | 1816 60 deg C. |
| *Candida albicans* | 60193 | + | − | + | + | + | +−− | + | − |
| *Candida guilliermondii* | 6260 | + | − | + | + | + | +−− | + | − |
| *Candida kefyr* | 4135 | + | − | + | + | + | +−− | + | − |
| *Candida kefyr* | 46764 | + | − | + | + | + | +−− | + | − |
| *Candida krusei* | 6258 | + | − | + | − | + | +−− | + | − |
| *Candida lusitaniae* | 42720 | + | − | + | − | + | +−− | + | − |
| *Candida parapsilosis* | 22019 | + | − | + | + | + | +−− | + | − |
| *Candida rugosa* | 58964 | + | +−− | +−− | − | + | +−− | +− | − |
| *Candida tropicalis* | 750 | + | − | + | + | + | +−− | + | − |
| *Candida tropicalis* | 13803 | + | − | + | + | + | +−− | + | − |
| *Candida tropicalis* | 42678 | + | − | . | + | + | +−− | + | − |
| *Candida utilis* | 9226 | + | − | + | +−− | + | +−− | + | − |
| *Candida viswanathii* | 22981 | + | − | + | + | + | +−− | + | − |
| *Chrysosporium keratinophilum* | 14803 | + | − | + | + | + | +−− | + | − |
| *Cladosporium castellani* | 24788 | + | − | + | + | + | +−− | + | − |
| *Cryptococcus neoformans* | 14116 | + | − | + | + | + | +−− | − | − |
| *Cryptococcus neoformans* | 32045 | + | − | + | + | + | +−− | − | − |
| *Cyathus stercoreus* | n6473 | +− | − | + | + | + | + | +− | − |
| *Entomophthora virulenta* | 14207 | +−− | − | +−− | − | + | +−− | − | − |
| *Epidermophyton floccosum* | 52066 | + | − | + | + | + | +−− | +− | − |
| *Filobasidiella neoformans* | 6352 | + | − | + | + | + | +−− | − | − |
| *Fusarium oxysporum* | 16322 | + | − | + | +− | + | +−− | + | + |
| *Geotrichum candidum* | 34614 | + | − | + | + | + | +−− | + | − |
| *Hansenula polymorpha* | 34438 | + | − | +− | − | + | +−− | + | + |
| *Histoplasma capsulatum* | 12700 | + | − | + | + | + | +−− | + | − |
| *Lipomyces starkeyi* | n11557 | + | − | + | +−− | + | +−− | + | − |
| *Metschnikowia bicuspidata* | 22297 | + | − | + | +− | + | + | + | − |
| *Microsporum racemosum* | 38556 | + | − | + | + | + | +−− | + | − |
| *Mucor rouxii* | 24905 | + | − | + | +−− | +−− | − | + | − |
| *Neurospora crassa* | 14692 | + | − | + | + | + | +−− | + | + |
| *Neurospora sitophila* | 36935 | + | − | + | + | + | +−− | + | + |
| *Paracoccidioides brasiliensis* | 48093 | + | − | + | + | + | +−− | +. | − |
| *Penicillium crysogenum* | 10106 | + | − | + | + | + | +−− | +− | − |
| *Penicillium digitatum* | 48113 | + | − | + | + | + | − | +− | − |
| *Penicillium notatum* | 9179 | + | − | + | + | + | +−− | +− | − |
| *Phycomyces blakesleeanus* | n1464 | +− | − | +− | − | +− | +−− | + | − |
| *Pityrosporum ovale* | 14521 | +−− | − | +− | − | + | + | + | − |
| *Pseudallescheria boydii* | 28169 | + | − | + | + | + | +−− | + | + |
| *Rhizopus oligosporus* | 22959 | + | − | +−− | − | +−− | − | + | − |
| *Rhodosporidium toruloides* | 10788 | + | − | + | + | + | +−− | − | − |
| *Rhodotorula rubra* | 9449 | + | − | + | + | + | + | − | − |
| *Saccharomyces cerevisiae* | 18824 | + | − | + | + | + | +−− | + | − |
| *Saccharomycodes ludwigii* | n12792 | + | − | + | + | + | +−− | + | − |
| *Schizosaccharomyces octosporus* | 4206 | + | − | + | + | + | +−− | + | − |
| *Sporothrix schenkii* | 14284 | + | − | + | + | + | +−− | + | − |
| *Taphrina deformans* | nT857 | + | − | + | + | + | +−− | + | − |
| *Torulopsis glabrata* | 2001 | + | − | + | + | + | +−− | + | − |
| *Tremella mesenterica* | 42219 | − | − | + | +−− | +− | − | + | − |
| *Trichophyton mentagrophytes* | 28185 | + | − | + | + | + | +−− | +− | − |
| *Trichophyton rubrum* | 28188 | + | − | + | + | + | +−− | + | − |
| *Trichosporon beigelii* | 28592 | +− | − | + | +− | + | +−− | − | − |
| *Trichosporon capitatum* | 10663 | − | − | +−− | − | +−− | − | + | − |
| *Ustilago maydis* | j1402 | − | − | + | +−− | + | +−− | + | − |
| *Verticillium dahliae* | 16535 | + | − | + | + | + | +−− | + | + |
| *Yarrowia lipolytica* | 18942 | +− | − | +−− | − | +−− | − | + | − |
| EXCLUSIVITY | | | | | | | | | |
| HUMAN/CaSKi | | − | − | − | − | − | − | +−− | − |
| *Staphylococcus aureus* | GT204 | − | − | − | − | − | − | − | − |
| *Escherichia coli* | 12036 | − | − | − | − | − | − | − | − |
| Stool RNA | | − | − | − | − | − | − | − | − |
| Wheat germ RNA | | − | − | +−− | − | − | − | +−− | − |
| *Candida albicans* | | | | | | | | | |
| 190-87 | | + | − | + | + | + | +−− | + | − |
| 266-87 | | + | − | + | + | + | +−− | + | − |
| *Candida guilliermondii* | | | | | | | | | |
| 350-87 | | + | − | + | + | + | +−− | + | − |
| 715-88 | | + | − | + | + | + | +−− | + | − |
| *Candida krusei* | | | | | | | | | |
| 842-88 | | + | − | + | +−− | + | +− | + | − |
| 939-88 | | + | − | + | +−− | + | +−− | + | − |
| *Candida (Yarrowia) lipolytica* | | | | | | | | | |
| 056584 | | +− | − | − | − | − | − | + | − |
| 125085 | | +− | − | − | − | − | − | + | − |
| *Candida lusitaniae* | | | | | | | | | |
| 121585 | | + | − | + | +−− | + | +−− | + | − |
| 121685 | | + | − | + | +−− | + | +−− | + | − |

TABLE 3-continued

| | | \multicolumn{8}{c}{DOTBLOT HYBRIDIZATION DATA} |
| NAME/STRAIN | | 1813 50 deg C. | 1813 60 deg C. | 1814 50 deg C. | 1814 60 deg C. | 1812 50 deg C. | 1812 60 deg C. | 1816 50 deg C. | 1816 60 deg C. |
|---|---|---|---|---|---|---|---|---|---|
| *Candida parapsilosis* | | | | | | | | | |
| 176-87 | | + | − | + | + | + | +−− | + | − |
| 754-88 | | + | − | + | + | + | +−− | + | − |
| *Candida (kefyr) pseudotropicalis* | | | | | | | | | |
| 100188 | | + | − | + | + | + | +−− | + | − |
| 999-88 | | + | − | + | + | + | +−− | + | − |
| *Candida tropicalis* | | | | | | | | | |
| 150-87 | | + | − | + | + | + | +−− | + | − |
| 210-87 | | + | − | + | + | + | +−− | + | − |
| *Torulopsis glabrata* | | | | | | | | | |
| 288-87 | | + | − | + | + | + | +−− | + | − |
| 334-87 | | + | − | + | + | + | +−− | + | − |
| *Cryptococcus albidus* | | | | | | | | | |
| 83-0085 | | + | − | + | + | + | +− | + | − |
| 85-0707 | | + | − | + | + | + | +− | + | − |
| *Cryptococcus laurentii* | | | | | | | | | |
| 82-0600 | | +−− | − | + | + | + | +−− | − | − |
| 87-0657 | | +−− | − | + | + | + | +−− | − | − |
| *Cryptococcus neoformans* A | | | | | | | | | |
| 151 | | + | − | + | + | + | +−− | − | − |
| 162 | | + | − | + | + | + | +−− | − | − |
| *Cryptococcus neoformans* B | | | | | | | | | |
| 184 | | + | − | + | + | + | +− | − | − |
| B3174a | | + | − | + | + | + | +− | − | − |
| *Cryptococcus neoformans* C | | | | | | | | | |
| 298 | | + | − | + | + | + | +− | − | − |
| B3185a | | + | − | + | + | + | +−− | − | − |
| *Cryptococcus neoformans* D | | | | | | | | | |
| 161 | | + | − | + | + | + | +− | − | − |
| 166 | | + | − | + | + | + | +− | − | − |
| ADDITIONAL ASPERGILLI AND PENICILLIUM | | | | | | | | | |
| *Aspergillus clavatus* | 9192 | + | − | + | + | + | +− | nt | nt |
| *Aspergillus niger* | 10535 | + | − | + | + | + | +− | nt | nt |
| *Aspergillus niger* | 16404 | + | − | + | + | + | +− | nt | nt |
| *Aspergillus niger* | 16880 | + | − | + | + | + | +− | nt | nt |
| *Aspergillus oryzae* | 14895 | + | − | + | + | + | +− | nt | nt |
| *Aspergillus repens* | 48521 | + | − | + | + | + | +− | nt | nt |
| *Penicillium chrysogenum* | 10002 | + | − | + | + | + | +− | nt | nt |
| *Penicillium expasum* | 7861 | + | − | + | + | + | +−− | nt | nt |
| *Penicillium italicum* | 48114 | + | − | + | + | + | +− | nt | nt |
| *Penicillium roquefortii* | 10110 | + | − | + | + | + | +− | nt | nt |
| ADDITIONAL BLASTOMYCES AND HISTOPLASMAS | | | | | | | | | |
| *Blastomyces dermatitidis* | 064571 | + | − | + | + | + | +−− | nt | nt |
| *Blastomyces dermatitidis* | 82-0741 | + | − | + | + | + | +−− | nt | nt |
| *Blastomyces dermatitidis* | CDCB44 | + | − | + | + | + | +−− | nt | nt |
| *Blastomyces dermatitidis* | NYS48 | + | − | + | + | + | +−− | nt | nt |
| *Histoplasma capsulatum* | CDCA28 | + | − | + | + | + | +−− | nt | nt |
| *Histoplasma capsulatum* | NYS211 | + | − | + | + | + | +−− | nt | nt |
| *Histoplasma capsulatum* | NYS214 | + | − | + | + | + | +−− | nt | nt |
| *Histoplasma capsulatum* | NYS215 | + | − | + | + | + | +−− | nt | nt |
| *Histoplasma capsulatum* | NYS216 | + | − | + | + | + | +−− | nt | nt |
| *Histoplasma capsulatum* | NYS232 | + | − | + | + | + | +−− | nt | nt |

What is claimed is:

1. A nucleic acid probe consisting of a nucleotide sequence complementary to at least 90% of a sequence comprising any 26 consecutive nucleotides within a probe selected from the group consisting of Probes 1415 (SEQ ID NO: 3), 1416 (SEQ ID NO: 4), IG707 (SEQ ID NO: 5), 1859 (SEQ ID NO: 15), 1858 (SEQ ID NO: 14), 1857 (SEQ ID NO: 10, 1812 (SEQ ID NO: 13), 1813 (SEQ ID NO: 11), 1814 (SEQ ID NO: 8), and 1816 (SEQ ID NO: 9), which probe hybridizes to the 18S rRNA or rDNA of fungi, but not to the rRNA or rDNA of human, bacteria, and wheat under the same hybridization conditions.

2. A nucleic acid probe consisting of a nucleotide sequence homologous to at least 90% of a sequence comprising any 26 consecutive nucleotides within a probe selected from the group consisting of Probes 1415 (SEQ ID NO: 3), 1416 (SEQ ID NO: 4), IG707 (SEQ ID NO: 5), 1859 (SEQ ID NO: 15), 1858 (SEQ ID NO: 14), 1857 (SEQ ID NO: 10, 1812 (SEQ ID NO: 13), 1813 (SEQ ID NO: 11), 1814 (SEQ ID NO: 8), and 1816 (SEQ ID NO: 9), which probe hybridizes to the 18S rRNA or rDNA of fungi, but not to the rRNA or rDNA of human, bacteria, and wheat under the same hybridization conditions.

3. A set of nucleic acid probes comprising at least two probes, wherein at least one of said probes is selected from the group consisting of probes 1417 (SEQ ID NO: 1), 1418 (SEQ ID NO: 2), 1415 (SEQ ID NO: 3), 1416 (SEQ ID NO: 4), 1542 (SEQ ID NO: 6), 1545 (SEQ ID NO: 7), IG707 (SEQ ID NO: 5), 1859 (SEQ ID NO: 15), 1860 (SEQ ID NO: 12), 1858 (SEQ ID NO: 14), 1857 (SEQ ID NO: 10), 1812 (SEQ ID NO: 13), 1813 (SEQ ID NO: 11), 1814 (SEQ ID NO: 8), 1816 (SEQ ID NO: 9), 936 (SEQ ID NO: 16), and 935 (SEQ ID NO: 17), and their complementary sequences, which probe hybridizes to the 18S rRNA or rDNA of fungi, but not to the rRNA or rDNA of human.

4. The nucleic acid probe of claim 1, wherein said nucleotide sequence is complementary to probe 1415 (SEQ ID NO: 3), 1416 (SEQ ID NO: 4), IG707 (SEQ ID NO: 5), 1859 (SEQ ID NO: 15), 1858 (SEQ ID NO: 14), 1857 (SEQ ID NO: 10), 1812 (SEQ ID NO: 13), 1813 (SEQ ID NO: 11), 1814 (SEQ ID NO: 8), or 1816 (SEQ ID NO: 9).

5. The nucleic acid probe of claim 2, wherein said nucleotide sequence is homologous to probe 1415 (SEQ ID NO: 3), 1416 (SEQ ID NO: 4), IG707 (SEQ ID NO: 5), 1859 (SEQ ID NO: 15), 1858 (SEQ ID NO: 14), 1857 (SEQ ID NO: 10), 1812 (SEQ ID NO: 13), 1813 (SEQ ID NO: 11), 1814 (SEQ ID NO: 8), or 1816 (SEQ ID NO: 9).

6. The set of nucleic acid probes of claim 3, wherein said set is selected from the group of probe pairs:
1417 (SEQ ID NO: 1) and 1542 (SEQ ID NO: 6),
1417 (SEQ ID NO: 1) and 1545 (SEQ ID NO: 7), 1418 (SEQ ID NO: 2) and 1542 (SEQ ID NO: 6),
1418 (SEQ ID NO: 2) and 1545 (SEQ ID NO: 7),
1416 (SEQ ID NO: 4) and 1812 (SEQ ID NO: 13),
1812 (SEQ ID NO: 13) and 1860 (SEQ ID NO: 12),
1857 (SEQ ID NO: 10) and 1860 (SEQ ID NO: 12),
1812 (SEQ ID NO: 13) and 936 (SEQ ID NO: 16),
1814 (SEQ ID NO: 8) and 1415 (SEQ ID NO: 3), and
1814 (SEQ ID NO: 8) and 1416 (SEQ ID NO: 4).

7. A nucleic acid probe consisting of a nucleotide sequence complementary to at least 90% of a sequence comprising any 26 consecutive nucleotides within a probe selected from the group consisting of probes 1417 (SEQ ID NO: 1), 1418 (SEQ ID NO: 2), 1542 (SEQ ID NO: 6), 1545 (SEQ ID NO: 7), and 1860 (SEQ ID NO: 12), which probe hybridizes to the 18S rRNA or rDNA of fungi, but not to the rRNA or rDNA of human.

8. A nucleic acid probe consisting of a nucleotide sequence homologous to at least 90% of a sequence comprising any 26 consecutive nucleotides within a probe selected from the group consisting of probes 1417 (SEQ ID NO: 1), 1418 SEQ ID NO: 2), 1542 (SEQ ID NO: 6), 1545 (SEQ ID NO: 7), and 1860 (SEQ ID NO: 12), which probe hybridizes to the 18S rRNA or rDNA of fungi, but not to the rRNA or rDNA of human.

9. The nucleic acid probe of claim 7, wherein said nucleic acid sequence is complementary to probe 1417 (SEQ ID NO: 1), 1418 SEQ ID NO: 2), 1542 (SEQ ID NO: 6), 1545 (SEQ ID NO: 7), or 1860 (SEQ ID NO: 12).

10. The nucleic acid probe of claim 8, wherein said nucleic acid sequence is homologous to probe 1417 (SEQ ID NO: 1), 1418 (SEQ ID NO: 2), 1542 (SEQ ID NO: 6), 1545 (SEQ ID NO: 7), or 1860 (SEQ ID NO: 12).

11. A nucleic acid probe consisting of a nucleotide sequence complementary to at least 90% of a sequence comprising any consecutive nucleotides within a probe selected from the group consisting of probes 936 (SEQ ID NO: 16) and 935 (SEQ ID NO: 17), which probe hybridizes to the 18S rRNA or rDNA of fungi, but not to the rRNA or rDNA of human.

12. A nucleic acid probe consisting of a nucleotide sequence homologous to at least 90% of a sequence comprising any 26 consecutive nucleotides within a probe selected from the group consisting of probes 936 (SEQ ID NO: 16) and 935 (SEQ ID NO: 17), which probe hybridizes to the 18S rRNA or rDNA of fungi, but not to the rRNA or rDNA of human.

13. A method for detecting a fungal organisms in a biological sample from a patient comprising the steps of:
   a) contacting said sample with at least one nucleic acid probe of any one of claims 2, 3, 7, or 8;
   b) imposing conditions on the sample and said nucleic acid probe to allow said probe to hybridize to 18S rRNA or rDNA of said fungal organism, if present in said sample, to form nucleic acid complexes; and
   c) detecting said nucleic acid complexes as an indication of the presence of said fungal organism in the sample.

14. The method of claim 13, wherein said nucleic acid probe in said contacting step is selected from the group of probes consisting of probes 1417 (SEQ ID NO: 1), 1418 (SEQ ID NO: 2), 1415 (SEQ ID NO: 3), 1416 (SEQ ID NO: 4), 1542 (SEQ ID NO: 6), 1545 (SEQ ID NO: 7), IG707 (SEQ ID NO: 5), 1859 (SEQ ID NO: 15), 1860 (SEQ ID NO: 12), 1858 (SEQ ID NO: 14), 1857 (SEQ ID NO: 10), 1812 (SEQ ID NO: 13), 1813 (SEQ ID NO: 11), 1814 (SEQ ID NO: 8), 1816 (SEQ ID NO: 9), and their complementary sequences.

15. The method of claim 13, wherein said nucleic acid probe in said contacting step comprises probe/primer 936 (SEQ ID NO: 16) and said detecting step comprises further contacting said sample with a second nucleic acid probe selected from the group of probes consisting of probes 935 (SEQ ID NO: 17), 1417 (SEQ ID NO: 1), 1418 (SEQ ID NO: 2), 1415 (SEQ ID NO: 3), 1416 (SEQ ID NO: 4), 1542 (SEQ ID NO: 6), 1545 (SEQ ID NO: 7), IG707 (SEQ ID NO: 5), 1859 (SEQ ID NO: 15), 1860 (SEQ ID NO: 12), 1858 (SEQ ID NO: 14), 1857 (SEQ ID NO: 10), 1812 (SEQ ID NO: 13), 1813 (SEQ ID NO: 11), 1814 (SEQ ID NO: 8), and 1816 (SEQ ID NO: 9).

16. The method of claim 15, further comprising the step of amplifying 18S rRNA or 18S rRNA gene sequences of said fungal organism by polymerase chain reaction before said contacting step.

* * * * *

UNITED STATES PATENT AND TRADEMARK OFFICE
CERTIFICATE OF CORRECTION

PATENT NO. : 5,324,632

DATED : June 28, 1994

INVENTOR(S) : William G. Weisburg et al.

It is certified that error appears in the above-identified patent and that said Letters Patent is hereby corrected as shown below:

Column 1, line 59, delete "barceremic" and insert therefor --bacteremic--;

Column 2, line 60, delete "alloy" and insert therefor --allow--;

Column 7, line 25, delete "; Inclusive" and insert therefor --inclusive--;

Column 8, line 65, after "turn", insert --,--;

Column 9 (Table 1), last line, delete "36252" and insert therefor --36232--;

Column 15 (Table 1), line 50, delete "151" and insert therefor --161--;

Column 15 (Table 2), line 76, delete "36252" and insert therefor --36232--;

Column 19 (Table 3), last line, delete "36252" and insert therefor --36232--;

Column 22 (Table 3), line 29, in the column entitled "1816 - 60 deg C." and along the line entitled "*Hansenula polymorpha*", delete "+" and insert therefor -- - --;

Column 30 (Sequence Listing), line 18, delete "289" and insert therefor --28--;

Column 29, line 47, after "10", insert --)--;

UNITED STATES PATENT AND TRADEMARK OFFICE
CERTIFICATE OF CORRECTION

PATENT NO. : 5,324,632

DATED : June 28, 1994

INVENTOR(S) : William G. Weisburg et al.

It is certified that error appears in the above-identified patent and that said Letters Patent is hereby corrected as shown below:

Column 29, line 59, after "10", insert --)--;

Column 31, line 21, after "1418", insert -- (--; and

Column 31, line 37, after "any", insert --26--.

Signed and Sealed this

Fifteenth Day of November, 1994

Attest:

BRUCE LEHMAN

Attesting Officer

Commissioner of Patents and Trademarks